United States Patent [19]

Kiczka

[11] Patent Number: 6,132,715
[45] Date of Patent: *Oct. 17, 2000

[54] METHOD OF INHIBITING BIOSYNTHESIS OF TUMOR NECROSIS FACTOR

[75] Inventor: Witold Kiczka, Princeton, N.J.

[73] Assignee: Nika Health Products Limited, Vaduz, Liechtenstein

[ * ] Notice: This patent is subject to a terminal disclaimer.

[21] Appl. No.: 08/476,561

[22] Filed: Jun. 7, 1995

Related U.S. Application Data

[62] Division of application No. 08/351,375, Feb. 13, 1995, abandoned, and a continuation-in-part of application No. 07/865,002, Apr. 8, 1992, Pat. No. 5,466,449, which is a division of application No. 07/459,738, filed as application No. PCT/US88/01785, May 26, 1988, Pat. No. 5,200,182.

[30] Foreign Application Priority Data

Jul. 13, 1992 [PL] Poland ................................. P-295273

[51] Int. Cl.$^7$ .................................................. A61K 38/47
[52] U.S. Cl. ..................... 424/94.61; 424/94.1; 435/183; 435/200
[58] Field of Search ................................ 424/94.1, 94.61; 435/183, 200

[56] References Cited

U.S. PATENT DOCUMENTS

| | | |
|---|---|---|
| 4,221,794 | 9/1980 | Simon et al. . |
| 4,457,919 | 7/1984 | Simon et al. . |
| 4,510,144 | 4/1985 | Hadden et al. . |
| 4,739,046 | 4/1988 | Di Luzio . |
| 4,744,984 | 5/1988 | Ragland . |
| 5,118,500 | 6/1992 | Hänel et al. ............................ 424/85.1 |
| 5,200,182 | 4/1993 | Kiczka ..................................... 424/94.5 |
| 5,314,816 | 5/1994 | Uerrmann et al. ....................... 435/188 |
| 5,317,019 | 5/1994 | Bender et al. ......................... 514/224.2 |
| 5,420,154 | 5/1995 | Christensen, IV et al. ............. 514/424 |
| 5,466,449 | 11/1995 | Kiczka ................................. 424/94.61 |

FOREIGN PATENT DOCUMENTS

| | | |
|---|---|---|
| 0238851 | 9/1987 | European Pat. Off. . |
| 4020 M | 4/1966 | France . |
| 2215201 | 8/1974 | France . |
| 55-33408 | 3/1980 | Japan . |
| 55-33409 | 3/1980 | Japan . |
| 55-43040 | 3/1980 | Japan . |
| WO 89/11924 | 11/1989 | WIPO . |
| WO 91/10731 | 7/1991 | WIPO . |

OTHER PUBLICATIONS

Annapurna Vyakarnam et al. "Tumour Necrosis Factors (α,β) Induced by HIV–1 in Peripheral Blood Mononuclear Cells Potentiate Virus Replication", *AIDS*, vol. 4, No. 1, pp. 21–27, 1990.

Katherine Bayston et al., "Bacterial Endotoxin and Current Concepts in the Diagnosis and Treatment of Endotoxaemia", *J. Med. Microbiol.*, vol. 31., pp. 73–83, 1990.

Dennis Stevens et al., "Gram–positive Shock", *Current Opinion in Infectious Diseases*, vol. 5, pp. 355–363, 1992.

Frank Berkowitz, "Bacterial Toxins in the Pathogenesis of Infections", *Current Opinion in Infectious Diseases*, vol. 4, pp. 332–337, 1991.

Philip Mackowiak, "Mechanisms of Fever", *Current Opinion in Infectious Diseases*, vol. 5, pp. 348–354, 1992.

Toshifumi Matsuyama et al., "Cytokines and HIV Infection: Is AIDS a Tumor Necrosis Factor Disease?", *AIDS*, vol. 5, #12 pp. 1405–1417, 1991.

Masahiko Ito et al., "Tumor Necrosis Factor Antagonizes Inhibitory Effect of Azidothymidine on Human Immunodeficiency Virus (HIV) Replication In Vitro", *Biochemical and Biophysical Research Communications*, vol. 166, No. 3, pp. 1095–1101, Feb. 14, 1990.

Katsutoshi Takada et al., "Binding of Lysozyme to Lipopolysaccharide Suppresses Tumor Necrosis Factor Production in Vivo", *Infection and Immunity*, vol. 62, No. 4, pp. 1171–1175, Apr. 1994.

Ana Coito, et al., "Anti–TNF–α Treatment Down–Regulates the Expression of Fibronectin and Decreases Cellular Infiltration of Cardiac Allografts in Rats", *The Journal of Immunology*, vol. 154, pp. 2949–2958, 1995.

*Primary Examiner*—Chhaya D. Sayala
*Attorney, Agent, or Firm*—Oliff & Berridge, PLC

[57] ABSTRACT

Dimerized lysozyme is used prophylactically or as a treatment for diseases associated with Tumor Necrosis Factor. Administration of the dimerized lysozyme by mouth, injection, an impregnated tampon, an antiseptive dressing, a gel or an ointment results in lowered Tumor Necrosis Factor concentrations. Therapy proved to be effective and very simple in the treatment of diseases which have a multi-factor etiology and pathogenesis.

10 Claims, 3 Drawing Sheets

METHOD OF INHIBITING BIOSYNTHESIS OF TUMOR NECROSIS FACTOR

This application is a Divisional of U.S. patent application Ser. No. 08/351,375, filed Feb. 13, 1995, now Abandoned, and a Continuation-in-Part of U.S. patent application Ser. No. 07/865,002, filed Apr. 8, 1992, now U.S. Pat. No. 5,466,449, which is a Divisional of U.S. patent application Ser. No. 07/459,738, filed Jan. 26, 1990, now U.S. Pat. No. 5,200,182, which is the U.S. National Stage of International Application Ser. No. PCT/US88/01785 filed May 26, 1998.

BACKGROUND OF THE INVENTION

The present invention relates to new medical uses of lysozyme dimer and to compositions containing such dimer. The new uses are related to treating certain dysfunctions; of natural defensive mechanisms.

Enzymes in their monomeric forms have been known already for a long time to be therapeutically effective in the treatment of various diseases.

Lysozyme was discovered by Fleming in 1922, but it was not before 1950 that its enzymatic functions were revealed. Since that time the compound has been the subject of intensive research and various therapeutic effects were reported. Among others, these were antiviral, antibacterial, anti-inflammatory and antihistaminic properties. The therapeutic use of lysozyme, however, has been rather limited due to the negative side effects of the monomeric form.

This limitation of the practical use of lysozyme and other therapeutically active enzymes was overcome in the late eighties when it was discovered that isolated dimerized forms of enzymes, while retaining all beneficial properties of known monomeric forms, exhibit no negative side effects when used in therapeutic doses. The antiviral and antibacterial compositions comprising as the active ingredient lysozyme dimer or other dimerized enzymes have been described in WO 89/11294. In that application it was reported that in in vitro tests the lysozyme dimer has inhibited proliferation of a number of bacterial strains cultivated on samples taken from patients in concentrations of 5–20 mg/ml of the culture. It was also reported there that the dimer was effective in treating canine parvovirus (CPV) infections when administered orally twice a day at a dose of 1–2 mg/kg of body weight.

As the research work by the inventor was continued, further attractive features of lysozyme dimers were found and new therapeutical uses of the drug were developed.

In clinical tests performed in order to confirm the antibacterial and antiviral effectiveness of lysozyme dimer it was surprisingly found out that the dimer is unexpectedly potent in curing acute forms of diseases of the digestive and respiratory tracts. Accordingly, new investigations were carried out in order to determine the effect of lysozyme dimer in those stages of different diseases in which the natural defensive mechanisms fail.

It is known that the bacterial toxins constitute one group of many virulence factors by which bacteria cause diseases. Some recent advances in the knowledge of bacterial toxins concern their interaction with the host's immune system. This interaction firstly results in immunomodulation and secondly in the release of cytokines and other mediators, which account for many physiologic disturbances caused by the toxins. The latter effect has been studied particularly in regard to actions of endotoxin, which plays an important role in the pathogenesis of gram-negative sepsis (see Bayston, D. F., Cohen, J.: Bacterial endotoxins and current concepts in the diagnosis and treatment of endotoxaemia; J. Med. Microbiol. 1990, 31:73–83). Although for long time a role of exotoxins in infections caused by Staphylococcus aureus and *Streptococcus pyogenes* has been known, it was the recognition of the staphylococcal toxic shock syndrome that led to the increased interest in exotoxins produced by these organisms.

Toxic shock is a severe illness characterized by high fever, hypotension, capillary leak, diffuse erythroderma, mucosal erythema, renal impairment, hypocalcemia, hypoalbuminemia and desquamation of a red skin rash. Many cases of toxic shock syndrome have been associated with the use of vaginal tampons during menstruation but the syndrome is increasingly described in non-menstrual settings in both sexes frequently after surgical procedures when the packing material is left in place (e.g. nasal packings following rhinoplasty or severe epistaxis). The staphylococcus strains isolated from the vagina of patients with toxic shock syndrome (TSS) have been shown to produce toxic shock syndrome toxin 1 (TSST-1), but the source of the microorganism producing TSST-1 may also be an inapparent infection. The initial bacteremia may be inapparent but weeks or months later it may lead to the development of localized infections. Concomitant with the presentation of such infections, there may be evidence of sepsis syndrome or septic shock. A rarer but more dramatic bacteremia may occur in the absence of any portal of entry or associated localized infections, and in these situations shock, endocarditis, disseminated intravascular coagulopathy and multiorgan failure may be prominent (see Stevens, D. L. et al.: Gram-positive shock; Current Opinions in Infectious Diseases 1992, 5:355–363).

Similar observations are known to also involve other gram-positive bacteria. For example *Streptococcus pyogenes* infection is associated with shock and has a mortality rate of 30%. *Streptococcus pyogenes* is a cause of pneumonia, which has been documented to be of a high level of resistance to penicillin and tendency of development of a shock syndrome. Moreover, patients with AIDS have a higher incidence of pneumococcal infections than the population as a whole.

Infections with gram-negative bacteria can also result in sepsis and septic shock. Gram-negative bacilli and vibrios are the source of the most important enterotoxins. Enterotoxin is a lipopolysaccharide (LPS) component of the outer membrane of gram-negative bacterial cell walls. Enterotoxins primarily affect the intestinal tract and usually cause diarrhoea. The most frequent infections with gram-negative bacteria among animals and humans are the infections with *Escherichia coli*. Considerable dehydration accompanying such infections may result in the death of the infected individual. According to WHO, acute diarrhoea kills approximately 3.2 million children in developing countries each year. About 30% of all sepsis cases are caused by gram-negative bacteria.

Sepsis due to infections with gram-positive and gram-negative bacteria is always a severe condition common in all countries. There are approximately 400,000 cases a year within the United States with a mortality rate of approximately 50%.

In recent years, sepsis and septic shock have been a subject of many publications. It has been observed that in the pathophysiology of septic shock, endotoxemia and other bacterial intoxication mediators play the major role. They include tumor necrosis factor (TNF), interleukin-1 (IL-1), interferon (IFN), Platelet-activity factor and eicosanoids (derivatives of arachidonic acid); the most important of these is TNF which has effects on metabolism as well as on the immune and phagocytic systems (see Berkowitz, F. E.: Bacterial toxins in pathogenesis of infections; Current Opinions in Infectious Diseases, 1991 4: 332–337). It was demonstrated that non-survivors of septic shock had higher concentrations of TNF and interleukin-1. Many authors have reported elevated levels of TNF-α in plasma of the septic shock patients and in their blood. It is pointed also out that the toxic effect of TNF-α may not depend as much on TNF concentrations as on its persistence within the body.

Many authors have investigated the possibility of modulation of cytokine cascade in sepsis and septic shock. The reported successful proposals involve use of monoclonal anti-TNF antibodies and neutralization of lipopolysaccharide with antilipopolysaccharide. The antibodies however do not enhance the bacterial clearance. Partially beneficial effects were also observed when agents such as dexamethasone and pentoxiphylline blocking TNF production by macrophages were used.

It is also known that also other cytokines contribute to septic shock. In this situation, the treatments that modulate the cytokine cascade in septic shock have the potential to interfere with the infection containment, since the host defense is dependent upon these same inflammatory cytokines. Finding the means for prevention of septic shock is of a top priority because of potential benefit to a large number of patients. Controlling the level of TNF seems to be essential for these purposes.

Similarly critical is the role of TNF in another defensive mechanism being a fever, which is a physiologic response to infection typical for virtually all higher animals and humans. Five pyrogenic cytokines (interleukin-1, TNF, interferon, interleukin-2 and interleukin-6) are currently recognized as the principal endogenous mediators of the febrile response, inhibiting preoptic warm-sensitive neurons that normally facilitate heat loss and suppress heat production in the human organism. Fever and its mediators have the capacity to harm both the invading organism and the host. Considerable data have been accumulated in recent years suggesting that interleukin-1, TNF and interleukin-6 mediate the pathophysiologic abnormalities of infections. Since the endogenous pyrogens contribute to the pathologic process of various infections both the mediators and febrile response are potentially deleterious to the host. The most convincing evidence in this regard has come from the studies of gram-negative sepsis. There is also the evidence that endogenous pyrogens mediate systemic and local manifestations of sepsis due to gram-positive bacteria, AIDS, spirochetal infections, meningitis, adult respiratory distress syndrome suppurative arthritis and mycobacteriosis. Although the cited data are in contrast to the observation that the febrile response itself heightens resistance to infection in experimental animals, nevertheless, preservation of the species, more than survival of the individual, is the essence of the evolutionary process. Conceivably, the deleterious systemic effects of pyrogenic cytokines on the outcome of overwhelming infections (e.g. gram-negative sepsis) are adapted as beneficial local effects of fever in less fulminant infections. Therefore by hastening the demise of hopelessly infected individuals, nature kills the individuals that are dangerous for the species. In such a way the species as a whole might be protected from epidemic diseases (see Mackowiak, P. A.: Mechanism of Fever; Current Opinions in Infectious Diseases, 1992, 5:348–354).

A fundamental concept of the pathogens of fever is that exogenous pyrogens, regardless of their origin or structure, cause fever by inducing host cells (primarily macrophages) to produce endogenous pyrogens. Accordingly, therapeutic methods based on the use of anti-endogenous pyrogen antibodies and endogenous pyrogen receptor antagonists may be effective. One of the possibilities is the blocking of biosynthesis of TNF. Studies in animals show that TNF might be produced before IL-1 and other cytokines in the cascade of response to infection. According to many scientists, inhibiting the biosynthesis of TNF also means stopping the biosynthesis of IL-1. But inhibiting the biosynthesis of TNF also means stopping the deleterious effects of some fulminant and hopeless infections.

TNF is also known to be one of the mediators of the inflammation processes. The inflammation in many instances is the first stage of a disease in the natural course of which a septic shock develops. In the situation where the continuity of tissues is broken, such as in wounds susceptible to infection, war-like wounds, especially abdominal wounds (peritonitis), diseases in the gastro-intestinal tract such as acute infections accompanying appendicitis, acute bacterial and viral infections as those seen in post-influenza pneumonia, neoplasmic diseases, especially in the phase of decomposition of tumors and the like, inflammation is a first symptom of the increase of TNF production. Controlling the TNF level therefore would be a desired treatment of such infections.

Even more sound is the role of TNF in AIDS itself. AIDS is characterized by a profound immunodeficiency. The hallmark of AIDS is a decreased number of CD4+ lymphocytes. The number of cells infected with HIV, the etiologic agent of AIDS—is relatively small ($\leq 1$ in 100–1000) even in the peripheral blood mononuclear cells (PBMC) of AIDS patients. While CD4+ lymphocytes are preferentially infected, these cells are not the exclusive targets of HIV infection. Recent evidence has shown that the spectrum of HIV target cells may be quite broad. Clear differences have been observed in the outcome of HIV infection in monocytes/macrophages versus T-lymphocytes. While the T-lymphocytes tend to be destroyed, monocytes/macrophages permit a persistent infection. HIV can therefore be harbored as reservoirs by monocyte/macrophages as well as other cells in the body. The monocyte/macrophage type of response to HIV infection could be responsible for established latency in the host; this response may also cause pathogenic sequelae resulting from soluble factors produced by the infected cells (see Toshifumi Matsuyama et al.: Cytokines and HIV infection: Is AIDS a Tumor Necrosis Factor disease?; AIDS 1991, 5:1405–1417). It was reported by many scientists that human T-cell lines infected with HTLV-1 are highly susceptible to HIV infection, demonstrating dramatic cytopathic effect in association with enhanced replication of HIV. In addition HIV infected cells are susceptible to damage by the supernatant of these cells. Assaying the viral titer after treatment with this supernatant revealed that the factor produced by T-cells (MT-2) enhanced the replication of HIV. The factor was identified as TNF-β and this finding is consistent with reports that T-cells (MT-2) produce TNF-β. The same effect was observed when using TNF-α. TNF-α and TNF-β enhanced the replication of HIV. It was also reported that HIV-infected T-cell lines and freshly isolated PBMC from HIV-infected individuals responded to TNF resulting in elevated levels. This suggests that the same enhancement of HIV expression is likely to occur in vivo. In fact, the enhancing activity of TNF could be neutralized by anti-TNF antibodies. The enhancement of HIV replication after treatment with TNF-α and TNF-α is up to 10 fold (see Vyakarnam, A. et al.: Tumor necrosis factors (α,β) induced by HIV-1 in peripheral blood mononuclear cells potentiate virus replication; AIDS 1990, 421–427).

It has also been confirmed that various cytokines can affect HIV production. By employing purified mononuclear phagocytes from normal peripheral blood, both IL-6 and TNF-α induction was observed within a few hours after exposure to HIV virus. This cytokine induction was also observed using heat-in-activated HIV. Based on many observations Toshifumi Matsuyama et al. (op.cit.) are convinced that AIDS represents a cytokine or TNF disease. In the cytokine network of AIDS, TNF-α and TNF-β appear to be crucial molecules enhancing the replication of HIV as well as inducing their own expression and that of other cytokines. TNF-α has been demonstrated to stimulate the release of other cytokines in various cell types, and is therefore to be a key cytokine of the cytokine cascade in the first defence mechanism.

It has been suggested that many of the symptoms associated with AIDS can be explained by the release of cytokines of different biological functions. Enhanced production of IL-1 and TNF-α, the two well known pyrogens could explain fever seen in AIDS patients. TNF-α may be involved in AIDS-associated cachexia. Both TNF-α and TNF-β work as immuno-modulators and effector molecules in monocyte-mediated cytotoxicity. Furthermore TNF is responsible for activation of immune response and can directly kill HIV-infected cells, thus enhancing replication of HIV. Also an immunologic mechanism has been proposed to explain CD4-T cell depletion in AIDS (Matsuyama et al., op.cit.). It is also reported that AIDS-related Kaposi's sarcoma is also induced by TNF-α:TNF-β can be produced from keratinocytes by physiological stimuli such as ultraviolet light, which may contribute to the induction of IL-6 in the skin and development of Kaposi's sarcoma in AIDS. In tests in vitro, TNF-α can damage myelin and oligodendrocytes; also some glioma-derived cell lines have been shown to be susceptible to the anti-proliferative effect of TNF-α. This may lead to the conclusion that the dysfunction of the central nervous system in AIDS patients is a result of TNF-α involvement. Several reports have shown that the serum levels of TNF-α and IL-1 are substantially elevated with the development of AIDS and ARC (AIDS related complex) while they fell within the range of healthy control values in tests of serum of asymptomatic carriers of HIV. According to Matsuyama et al. (op.cit.), IDS is as much a TNF disease as it is a HIV disease. It shows that gaining a control over TNF induction may lead to establishing effective therapy for AIDS patients.

SUMMARY OF THE INVENTION

The following basic findings allowed to solve the above described problems and to find new therapeutical uses of lysozyme dimer under the above described pathological conditions:
1. Lysozyme dimer inhibits the synthesis of TNF,
2. Lysozyme dimer stimulates the synthesis of IFN-α,
3. Lysozyme dimer enhances the phagocytic activity.

Accordingly, it was an object of the present invention to provide pharmaceutical formulations therapeutically useful in the treatment of diseases associated with excessively high levels of TNF (tumor necrosis factor) as described above.

Another object of the present invention was to provide pharmaceutical compositions useful in the prophylaxis of diseases associated with excessively high levels of TNF as described above.

Still a further object of the present invention was to provide pharmaceutical formulations and hygiene products useful in the therapy and prevention of diseases associated with increasing and excessively high levels of TNF.

According to the invention, the objects as set up above can be reached by the following new uses of the dimerised form of lysozyme, and by new pharmaceutical formulations containing lysozyme dimer as the active ingredient:

the use of lysozyme dimer for the manufacture of a medicament for inhibiting the biosynthesis of Tumor Necrosis Factor in animals and humans;

the use of lysozyme dimer for the manufacture of a pharmaceutical preparation for the treatment of diseases associated with excessively high levels of Tumor Necrosis Factor;

the use of lysozyme dimer for the manufacture of a pharmaceutical preparation for the prophylaxis of diseases associated with excessively high levels of Tumor Necrosis Factor;

the use of lysozyme dimer for the manufacture of a medicament for controlling HIV-induced release of Tumor Necrosis Factor in asymptomatic carriers and AIDS-related complex patients;

the use of lysozyme dimer for the manufacture of pharmaceutical compositions for the treatment of AIDS.

the use of lysozyme dimer for the manufacture of a pharmaceutical preparation for the prevention and/or treatment of sepsis and septic shock;

the use of lysozyme dimer for the manufacture of a pharmaceutical preparation for the prevention and/or treatment of cachexia;

the use of lysozyme dimer for the manufacture of a pharmaceutical preparation for the prevention and/or treatment of fever;

injections comprising lysozyme dimer in an amount of 0.01–10 mg/ml, preferably 0.1–1.0 mg/ml of an apyrogenic sterile composition comprising a physiologically acceptable solvent and a pharmaceutically approved preservative;

injections as above for i.v. administration in a single or repeated dose of 0.02 mg/kg of body weight;

tampons and antiseptic dressings impregnated with, and ointments or gels comprising effective doses of lysozyme dimer for the prevention of sepsis and septic shock and for the treatment of infected wounds;

vaginal tampons impregnated with an effective dose of lysozyme dimer for use during menstruation.

As a dimerised form of lysozyme, the isolated purified lysozyme dimer is preferably used. For some applications it is possible to employ compositions which besides lysozyme dimer also contain small fractions of trimer and higher oligomers of the enzyme.

The injections according to the present inventions may also be administered intramuscularly and hypodermically. In some applications it may be also appropriate to administer the same liquid composition (simultaneously or independently) intrauterinely and intraudderly—or locally—eventually together with other topical preparations.

Preferred apyrogenic sterile compositions comprising at least one physiologically acceptable solvent and/or at least one pharmaceutically approved preservative consist of apyrogenic sterilized water or PBS water solution as a solvent and thiomersal as an approved preservative for protein pharmaceutical preparations.

The dimerised form of lysozyme is obtainable in a process of controlled polymerization of the enzyme monomer followed by careful purification, in particular the removal of the monomeric form having the reported toxic side effects and of trimers and higher oligomer fractions of the post reaction mixture. Any known method of polymerization may be useful for obtaining the dimeric form of the enzyme. One manufacturing process comprising purification steps has been described in WO 91/10731.

Previous pre-clinical tests of lysozyme dimer did not reveal any mutagenic nor teratogenic effects, and no or only very slight tolerance effects. Single dose toxicity at oral/dermal application $LD_{50}$ was unmeasurable (>2000 mg/kg), at i.v. application $LD_{50}$ was >1000 mg/kg.

The presently disclosed new application of lysozyme dimer proved to have solid grounds in in-vitro tests and to be effective in in-vivo clinical applications. Some comparative studies have also been conducted.

It is believed that the inhibiting effect on the release of TNF proves so effective due to the broader spectrum of activity of the lysozyme dimer, namely its ability to induce IFN release and its enhancing effect on phagocytosis. The two properties just mentioned are important factors in the natural defensive mechanisms. Accordingly, the therapeutic and prophylactic effects of the above identified new uses of lysozyme dimer are supported by its strengthening effect on the natural defensive mechanisms.

BRIEF DESCRIPTION OF THE DRAWING

The present invention will be further explained in the examples in which reference will be made to the accompanying drawings graphically illustrating the test results of particular interest.

DETAILED DESCRIPTION OF PREFERRED EMBODIMENTS

EXAMPLE 1

In order to determine the immunoactivity of the lysozyme dimer, an assay in human peripheral blood lymphocytes with FACS analysis has been employed.

Mitogenic stimulation in human peripheral lymphocytes is a well established method to test reactivity of the most important cells of the immune system. To test influences of therapeutical substances on the activation and proliferation of lymphocytes from healthy blood donors, the mitogen is added in a suboptimal dose and the lymphocyte response is finally measured quantitatively with immunorelevant parameters. The results are compared with the control value measured without medication.

To stimulate lymphocytes, ConA in a concentration of 20 $\mu$g/ml of medium was used. Initial cell concentration was $10^6$ cells/ml. The short-time cultures in a $CO_2$ incubator was carried out during one (IL-2 receptors on lymphocytes and HLA-Dr) or two days (all other tests). The following parameters have been measured as criteria for cellular activation:

neopterin (Marker for immune activation)

β-2-microglobulin (also an activation marker)

shed interleukin-2 (T-helper lymphocyte derived autocrine and paracrine substance) receptors interleukin-6 (cellular differentiation hormone)

tumor necrosis factor—TNF (vasoactive, multipotent interleukin)

interferon-α (differentiation factor especially for B-lymphocytes)

thymidine kinase (enzyme, upregulated in proliferation cells)

lymphocyte interleukin-2 receptor (acceptor molecule for autocrine and paracrine IL-2)

lymphocyte Ki-67 (antigen expressed in activated and proliferating cells)

lymphocyte HLA-Dr (class II histocompatibility antigen upregulated during immune reaction).

The following observations regarding cell products were made in the culture supernatant:

Neopterin—produced by T-lymphocytes during the immune response and in stimulated cultures—in the present experiments was not markedly elevated by the lysozyme dimer above the control value in ConA stimulated cells without the tested dimer. With increased concentration of the tested dimer, the neopterin values were slightly higher.

Similarly, β-2-microglobulin values in all concentrations of the lysozyme dimers fluctuated around the control value.

IL-2 receptors—being shed from the lymphocyte surface during culture and giving information about total IL-2 receptor turnover—were on a comparable level with the IL-2 receptors on the lymphocyte surface (reported below) and showed a clear suppression at the highest concentration of the tested dimer.

Interleukin-6 showed a clear tendency to dose-dependent higher values in higher concentrations. This molecule is very important in hematopoiesis, cell differentiation and immune reaction. In the test, the first three values had to be extrapolated, since the highest standard was only 2000 pg/ml.

The results relating to the remaining molecules are shown in Table 1 below. Unlike the Interleukin-6, the TNF-α was unexpectedly

TABLE 1

Influence of lysozyme dimer on the human peripheral blood lymphocytes

| No  | Sample      | HLA-Dr/CD3 | IL-2 Rec | Ki-67/CD8 | Ki-67/CD4 |
|-----|-------------|------------|----------|-----------|-----------|
|     | Control     | 3.3        | 8.9      | 6.0       | 2.7       |
| 1.  | 1 mg/ml     | 2.2        | 2.6      | 4.8       | 5.3       |
| 2.  | 0.3 mg/ml   | 1.9        | 6.3      | 4.1       | 3.0       |
| 3.  | 0.1 mg/ml   | 3.0        | 6.1      | 6.5       | (6.9)     |
| 4.  | 33 μg/ml    | 3.0        | 5.9      | 6.3       | 3.0       |
| 5.  | 10 μg/ml    | 3.4        | 6.0      | 7.7       | 3.7       |
| 6.  | 3.3 μg/ml   | 2.4        | 5.0      | 7.5       | 3.7       |
| 7.  | 1 μg/ml     | 2.5        | 4.9      | 7.0       | 4.1       |
| 8.  | 0.3 μg/ml   | 3.3        | 5.8      | 7.5       | 3.9       |
| 9.  | 0.1 μg/ml   | 2.8        | 4.0      | 7.9       | 3.8       |
| 10. | 33 ng/ml    | 3.1        | 4.6      | 8.0       | 4.1       |

| No  | Sample      | TNF    | Thym.-Kinase | IFN-α |
|-----|-------------|--------|--------------|-------|
|     | Control     | 205.11 | 9242         | 4.97  |
| 1.  | 1 mg/ml     | 38.07  | 923          | 8.81  |
| 2.  | 0.3 mg/ml   | 17.19  | 10914        | 9.44  |
| 3.  | 0.1 mg/ml   | 13.75  | 7254         | 17.96 |
| 4.  | 33 μg/ml    | 36.11  | 9525         | 3.67  |
| 5.  | 10 μg/ml    | 22.22  | 5492         | 7.54  |
| 6.  | 3.3 μg/ml   | 54.91  | 5198         | 6.26  |
| 7.  | 1 μg/ml     | 18.47  | 5840         | 33.91 |
| 8.  | 0.3 μg/ml   | 14.47  | 6839         | 10.07 |
| 9.  | 0.1 μg/ml   | 94.16  | 3672         | 4.97  |
| 10. | 33 ng/ml    | 172.46 | 7312         | 10.07 | present in culture supernatants in dramatically reduced concentrations, except the last two dilution steps, which proved to be ineffective in suppression of TNF concentration.

Thymidine kinase is measured in the lymphocyte cytoplasma after freezing and thawing of the cell pellet. The thymidine kinase is upregulated in dividing cells making it a good marker for cell proliferation. Table 1 data show a depression by the highest tested lysozyme dimer concentrations; in the other dilution steps, no clear tendency can be seen. Interferon-α, in turn, under the same conditions shows values above the control value of ConA alone at higher concentrations. A visible increase occurs from the second value to the third dilution.

Lymphocyte markers:

HLA-Dr/CD3, being a histocompatibility marker, is expressed on activated T-lymphocytes during the immune reaction. The results obtained show a certain percentage of activated T-cells in the control culture; with various concentrations of lysozyme dimer in the cultures, the values vary around the control value.

IL-2 receptors on lymphocytes: interleukin-2 is a cytokine produced by T-helper lymphocytes after activation through IL-1. IL-2 is autocrine and paracrine. T-helper lymphocytes not only produce IL-2 but are also stimulated to proliferation by this molecule. The receptors for IL-2 at the surface of T-helper lymphocytes are upregulated upon activation. Table 1 shows that at highest concentration of lysozyme dimer there is a marked suppression of the IL-2 receptors on lymphocytes, while the remaining values do not differ more than within the biological bandwidth. Table 1 also contains data related to Ki-67/CD8 and Ki-67/CD4. Ki-67 is a proliferation molecule appearing in cells undergoing mitosis. Ki-67 is an important parameter to assess stimulated cells and in tumor diagnosis. In the reported results, a slight inhibition of cell proliferation is seen in Ki-67 suppressor (CD8) cells with the highest two doses of lysozyme dimer. In helper (CD4) lymphocytes with the highest dose, there appears to be substantial increase in the percentage of positive cells. With lower doses, the percentage of cells expressing Ki-67/CD4 is slightly higher than the control value.

Figure 1:
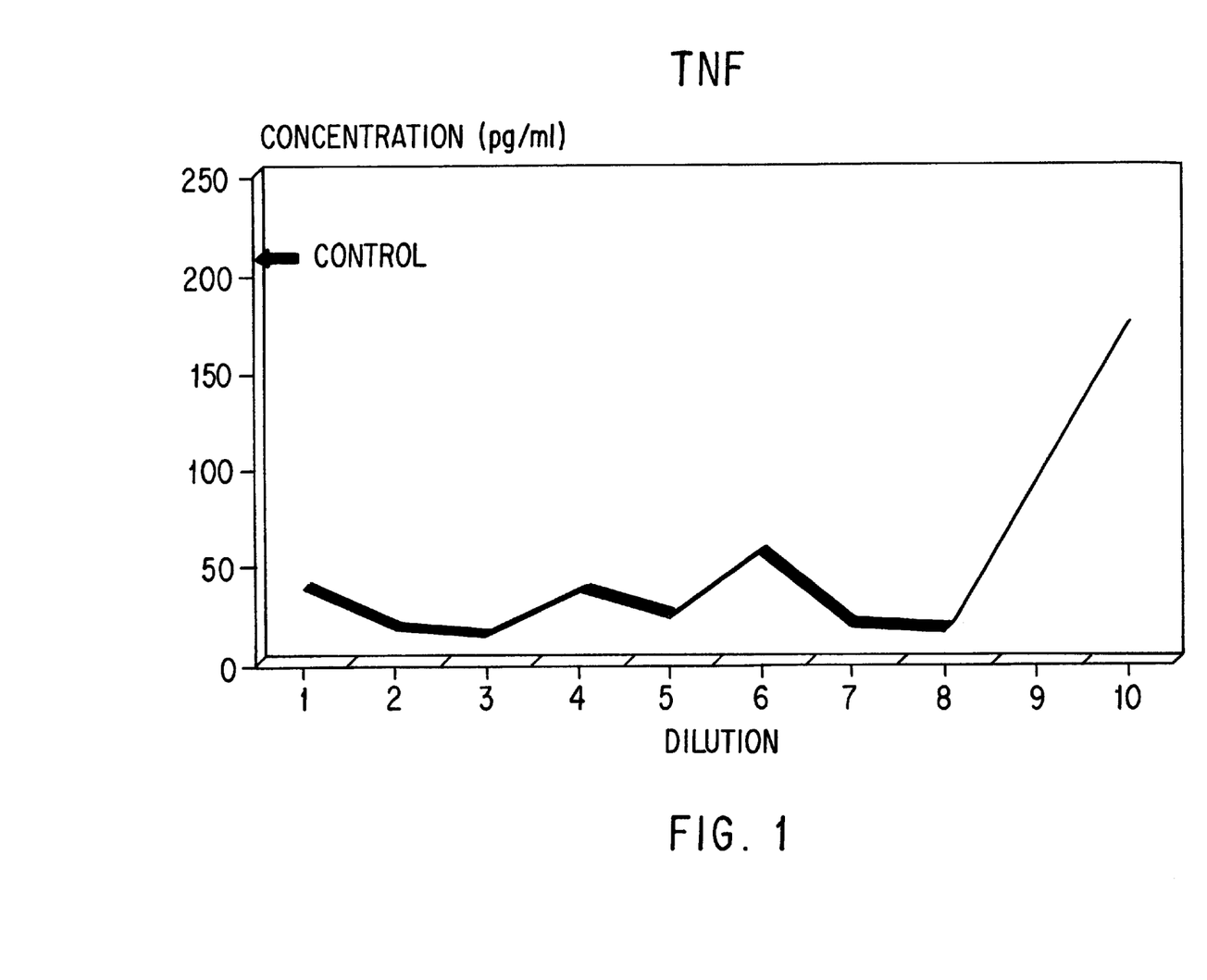
FIG. 1 illustrates an in-vitro suppression of TNF release in a lymphocyte culture suboptimally stimulated with ConA in the presence of lysozyme dimer in different dilutions.
Figure 2:
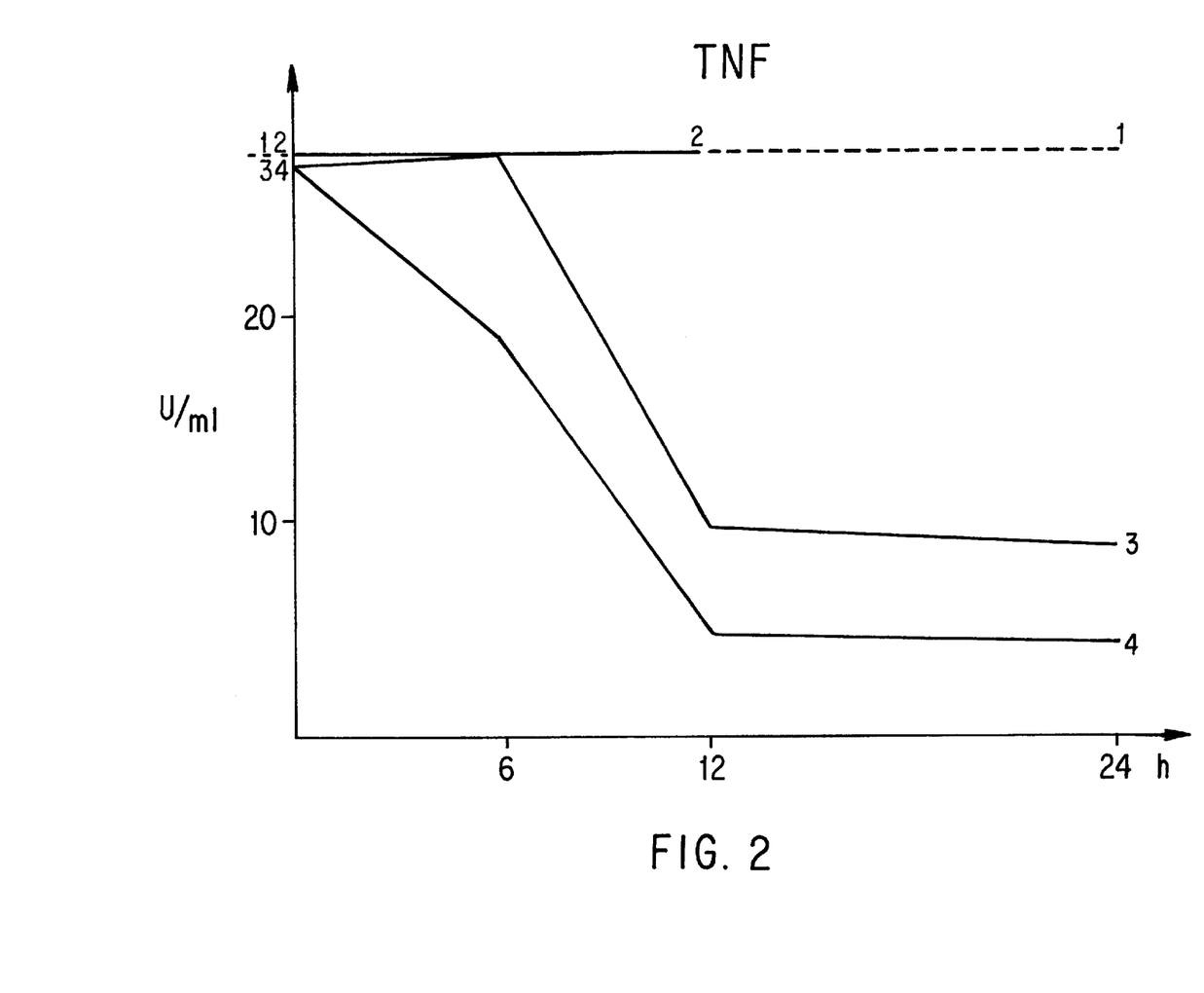
Figure 3:
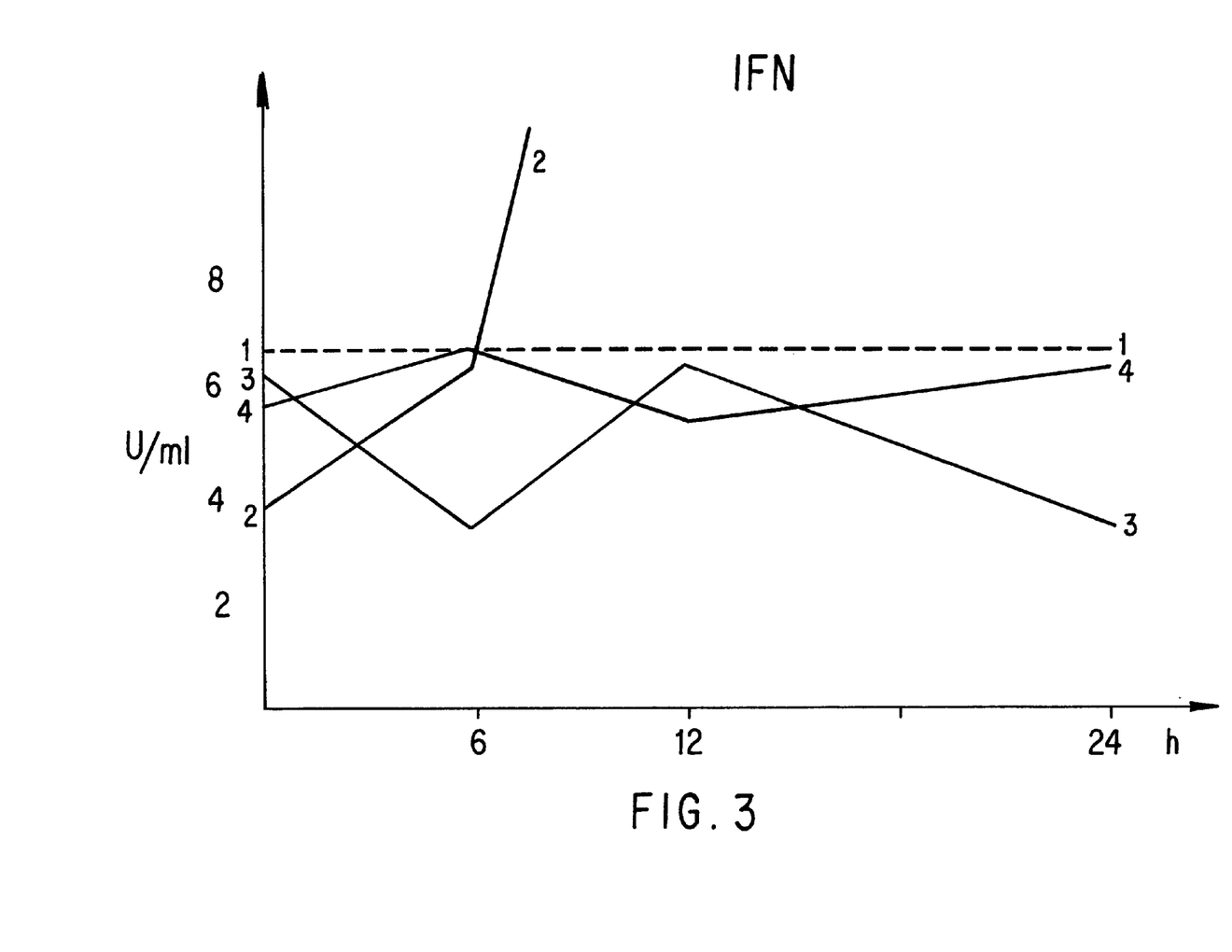

The marked suppression of TNF is shown in FIG. 1.

The immunological parameters listed above and chosen by their potential importance in the immune response were analyzed with the method based on measuring the influence of a tested substance on suboptimally Concanavalin A (ConA) stimulated human peripheral lymphocytes. The method being well established, sensitive and allowing to evaluate many different parameters. At some 20 concentrations of lysozyme dimers there are marked differences of the test results as compared to the values of lymphocytes stimulated with ConA alone, while as regards for example TNF and IFN-a, the observed effects are generally within the range of all tested dilutions.

EXAMPLE 2

Laboratory tests have been performed to determine the effect of lysozyme dimer on the phagocytic activity of milk and blood cells in vitro. It was earlier determined that in the standard in-vitro test, lysozyme dimer does not inhibit proliferation of the microorganisms isolated from the infected mammary glands of cows. As the clinical use of intraudderly and simultaneously intravenously administered lysozyme dimer effectively eliminates the infection of the mammary glands in cows, it was clear that the main antibacterial mechanism in mammary glands of cows is phagocytosis. Accordingly, blood and milk of both healthy and infected cows were used in in-vitro tests aiming to determine the effect of lysozyme dimer on phagocytosis. For comparison, the experiments were conducted with the same concentration of substance tested and the same incubation time using the cells isolated from healthy and infected cows or even from an infected and a healthy section of the mammary gland of the same cow, in order to eliminate individual response differences.

In the tests performed, both the purified dimeric form and a mixture of dimer and small fractions of trimers and higher oligomers of lysozyme were added to the blood or milk of the healthy and infected cows in concentrations of 25—0.25 pg/ml and the mixture was incubated at 37° C. for 0.5–24 hours. The percentage of phagocytizing cells (phagocytosis index according to the method of Wisniewski et al., Zycie wet. 1994 69:168) and the percentage of granulocytes Nitroblue tetrazolium test-positive (according to the method of Park, B., Lancet, 1968, 22:532) were determined for each sample.

The lysozyme dimer enhances phagocytic activity of leukocytes in the in-vitro tests. The effects are dependent on the dose and on the incubation time. Higher concentrations of lysozyme dimer are necessary to activate milk leukocytes than blood leukocytes. Excessively high concentrations of the dimer slightly reduce phagocytic activity in-vitro. Selected results—mainly showing that as long as the post-polymerization reaction mixture does not contain any cytotoxic monomeric form of the dimer, comparable results are obtained for highly purified and less pure dimerized lysozyme—are shown in the following Tables 2 and 3 in which a term "lysozyme dimer+" is used to indicate a composition containing a small fraction of trimers and higher oligomers of lysozyme as mentioned earlier in the specification.

TABLE 2

Effect of lysozyme dimer on phagocytic activity of milk leukocytes from healthy cows (concentration of the dimer 20 μg/ml, incubation time 3 hours)

| | | Healthy cow milk leukocytes | |
|---|---|---|---|
| Indicator | preparation | Cow No. 477 | Cow No. 463 |
| % phagocytosis | control | 77.8 | 80.0 |
| | lysozyme dimer + | 100 | 100 |
| | lysozyme dimer | 92.6 | 100 |
| phagocytosis index | control | 2.7 | 4.1 |
| | lysozyme dimer + | 4.4 | 6.4 |
| | lysozyme dimer | 4.8 | 8.4 |
| % reduction NBT | control | 3.4 | 2.5 |
| | lysozyme dimer + | 5.7 | 3.8 |
| | lysozyme dimer | 3.4 | 6.8 |

TABLE 3

Effect of lysozyme dimer on the phagocytic activity of milk leukocytes from infected cows (concentration of the dimer 20 μg/ml, incubation time 30 min.)

| | | Infected cow (No.490) milk leukocytes | |
|---|---|---|---|
| Indicator | preparation | infected*/ section | healthy section |
| % phagocytosis | control | 98 | 58 |
| | lysozyme dimer + | 98 | 90 |
| | lysozyme dimer | 100 | 100 |
| phagocytosis | control | 10.9 | 2.7 |

TABLE 3-continued

Effect of lysozyme dimer on the phagocytic activity of milk leukocytes from infected cows (concentration of the dimer 20 µg/ml, incubation time 30 min.)

| | | Infected cow (No.490) milk leukocytes | |
|---|---|---|---|
| Indicator | preparation | infected*/ section | healthy section |
| index | lysozyme dimer + lysozyme | 8.7 | 14.9 |
| | dimer | 10.9 | 8.9 |
| % reduction NBT | control lysozyme dimer + lysozyme | 4.2 | 4.2 |
| | | 5.9 | 8.4 |
| | dimer | 5.5 | 7.0 |

*/ = on set of inflammation; cow not treated

It is clear that the degree of purification of lysozyme dimer has no marked effect on the observed phagocytic activity of milk leukocytes. It may appear further that the effector cells may be granulocytes.

In the further examples, results of in-vivo studies are reported. For the clinical tests, the formulation of 2 mg of lysozyme dimer in 10 ml of PBS solution was used. This preparation is referred to as KLP-602.

EXAMPLE 3

When administered intravenously, KLP-602 was shown to stimulate phagocytic activity of blood granulocytes in healthy and sick calves and in healthy foals as well as in milk cows following intraudder application. The effect is manifested through an increased number of neutrophils and increased ability to absorb staphylococcus and to reduce NBT. This phenomenon occurs primarily during the first 12–24 hours following the injection of the preparation. The effect of KLP-602 upon phagocytic activity in the udder depended upon the dose and the form of the drug and the response of the individual animal.

EXAMPLE 5–7

Lysozyme dimer was used in the therapy of infectious diseases of cattle, pigs, horses and dogs. In different doses and at different time intervals, the preparation was administered intravenously, intramuscularly, subcutaneously, intraudderly and intrauterinely. The medication was administered to 346 cows, 274 calves, 110 sows and male pigs, 294 piglets, 709 sucking piglets, 35 foals and 107 dogs. Alternative treatment was applied as a control. Due to the nature of the test animals, none was left without therapeutical treatment for morality reasons. Nevertheless, the conclusions could be drawn in comparison to the clinical picture of the treated diseases known from veterinary literature.

EXAMPLE 5

KLP-602 was most effective in the treatment of diseases affecting pigs. 100% or nearly 100% of animals recovered from the following diseases: post-partum agalactia (MMA syndrome), dysentery, pyometritis, influenza and colibacillosis. Application of the medicament in cases of edema disease and bronchopneumonia gave slightly less prominent but still significantly better results than those obtained by alternative therapies. Prompt recession of diarrhoea (usually during the first 24 hours) and fever as well as reappearance of milk secretion of particular importance in cases of post-partum udder and uterine inflammations (saving the life of the piglets) could be observed. The effectiveness of KLP-602 therapy in comparison to alternative treatments is shown in Table 4 below.

EXAMPLE 6

When treated with KLP-602, 100% of foals suffering from enteritis and 83.3% of foals suffering from bronchopneumonia have recovered faster than the control group with known preparations.

EXAMPLE 7

KLP-602 was tested in the treatment of some diseases in dogs, such as folliculitis (100% effective), infection of the upper and lower respiratory tracts and infection of gastrointestinal tracts manifesting itself through diarrhoea. Prevalent in this group was parvovirosis, which is known to be practically an incurable disease. Nevertheless, a recovery rate of about 75% was observed in parvovirosis cases.

In the tests performed with the animals affected with naturally occuring diseases, as described above, several important observations were made:

1. The therapy proved to be effective and very simple in treatment of diseases which have a multi-factor etiology and pathogenesis (such diseases are prevalent in animal populations and are hard to handle especially in the breeding farms where epidemic spreading of diseases is very easy). Such findings prove the modulating effect of the lysozyme dimer on the natural defensive mechanisms.

TABLE 4

| Animals treated with KLP-602 | | | | | | Animals treated with other prepartions | | | |
|---|---|---|---|---|---|---|---|---|---|
| No. of cases | Duration (days) | Recovered number | % | Not recovered number | % | No. of cases | Preparation used | Duration | Recovery % |
| I. Colibacillosis of piglets | | | | | | | | | |
| 434 | 1–2 | 421 | 97 | 13 | 3 | 400[x] | antibiotics glucose, Vit.B | 3–5 | 75–80[x] |
| II. Dysentery of pigs | | | | | | | | | |
| 29 | 1–2 | 29 | 100 | — | — | 219 | antibiotics STOLMED, RIDOWET | 5–9 | 75 |

TABLE 4-continued

| | Animals treated with KLP-602 | | | | | Animals treated with other prepartions | | |
|---|---|---|---|---|---|---|---|---|
| No.of cases | Duration (days) | Recovered number | % | Not recovered number | % | No.of cases | Preparation used | Recovery Duration | % |
| III. Post-partum agalactia | | | | | | | | | |
| 30 | 1–2 | 30 | 100 | — | — | 40[x] | antibiotics cortisone, sulfamide | 3–5 | 80[x] |
| IV. Influenza of piglets | | | | | | | | | |
| 38 | 1–5 | 38 | 100 | — | — | 200[x] | antibiotics (latent formulations) | 3–9 | 60–80[x] |
| V. Morbus oedematosus | | | | | | | | | |
| 82 | 1–3 | 78 | 95 | 4 | 5 | 120[x] | antibiotics penicillin, tetracycline Vit. B, fluids + glucose | 3–6 | 60[x] |

[x]approximate data

2. The therapy proved to be effective in diseases which involve in their natural course the presence of endotoxic shock or other disorders such as high and long-lasting fever, affecting the status of an animal for long period of time after recovery and thus extremly detrimental for the animals such as horses (foals)—bred for races and other sports, as well as those bred mainly for the food industry, in which case the production costs are the critical issue. Quick recoveries will allow significant reduction of costs for the treatment of such diseases.
3. Results observed in vivo confirm suppressed levels of TNF in various naturally occuring infections treated with lysozyme dimers and thus support the invention as claimed.

EXAMPLE 8

The effect of lysozyme dimer on the activity of antibiotics against various different microorganisms was studied in order to select the bacteria for further tests, to determine the doses of antibiotics most effective for the selected microorganisms and to find the range of the lysozyme dimer concentrations within which the expected effects will be observed. In the experiments, two lots of lyophilized purified lysozyme dimer were used, one produced in 1991 and another one produced in 1992. In the experiments, antibiotics available on the Polish market, as supplied by Polfa, a Polish manufacturer of the drugs, such as penicillin, neomycin, erythromycin, cephalosporine (SEFRIL), were used.

The antibiotics to be tested were suspended in a buffered NaCl-solution (PBS-Biomed) or in a bovine serum. A lysozyme dimer was then added to the suspension in such a manner that in the tested samples the concentration of the dimer was always 5 µg/ml. The concentrations of the antibiotics being tested were different in each test due to varying sensibility of the microorganisms used.

The effect of the antibiotic alone or in combination with a lysozyme dimer was tested in a PBS or bovine serum suspension in vitro on *Escherichia coli, Salmonella enteritidis, Staphylococcus aureus* and *Streptococcus uberis* isolated from sick animals. Laboratory strains of *Sarcina lutea* 9341 ATCC and *Staphylococcus aureus* 209 P were also used in the experiments.

Due to the preliminary character of the tests, each antibiotic was tested against 1, 2 or 3 different kinds of bacteria as follows:
1. Preparation of the plates A 0.05 ml portion of an 18 hours broth culture of the bacteria strain to be tested was added to a 14 ml sample of enriched agar (Biomed). The mixture was stirred and poured out on a plate of 10 mm diameter. After cooling and solidification of the agar, sterile cylinders were placed thereon, and the cylinders were filled with the antibiotic solutions to be tested.
2. Preparation of the antibiotic solutions A 10 mg sample of the antibiotic to be tested was initially dissolved in PBS; next, the required volume of this solution was added to the predetermined volume of PBS or bovine serum so as to obtain a concentration of the antibiotic as close as possible to MIC (minimal inhibitory concentration); solutions of 3 different concentrations were always prepared.
3. Preparation of the lysozyme dimer solution 10 mg of lyophilized lysozyme dimer was initially dissolved in 10 ml of PBS. Further dilutions were prepared with either PBS or with bovine serum and added to the antibiotic solutions prepared earlier as described above. The following combinations were tested:
antibiotic/PBS
antibiotic/PBS+lysozyme dimer
antibiotic/serum
antibiotic/serum+lysozyme dimer The concentration of antibiotic was the same in each cylinder; the concentration of the lysozyme dimer was 5 µg/ml. After the cylinders were filled with the solutions, the plates were kept at room temperature for 2 hours; then, the cultures were incubated at 37° C.
4. Reading the results and evaluating the activity:

The plates were removed from the heater after 18 hours of incubation, and the diameter of the bacteria growth inhibition zone (lack of colonies) was measured around the cylinders.

No difference was found in the size of bacteria growth inhibition zones around the cylinders filled with the antibiotic suspensions in PBS without and with addition of lysozyme dimer in a concentration of 5 µg/ml. The size of the inhibition zone, however, decreased around the cylinders filled with the antibiotic suspension in bovine serum, but increased—around those filled with the antibiotic+lysozyme dimer suspensions in bovine serum. The zones were bigger than those seen around cylinders filled with PBS suspensions as well as bigger than those around cylinders filled with serum suspensions of antibiotics alone, free of lysozyme dimer.

The phenomenon occured in the tests with penicillin used against *Sarcina lutea*. Ampicillin showed a synergism in combination with lysozyme dimer in inhibiting in vitro growth of *Escherichia coli, Salmonella enteritidis* and *Staphylococcus epidermidis*. It was noted that there is an increase of activity of erythromycin in the presence of lysozyme dimer against *Staphylococcus aureus* 209 P and *Streptococcus uberis* as well as of SEFRIL—against *Staphylococcus aureus* 209 P. *Escherichia coli* and *Salmonella enteritidis* were resistant to this antibiotic.

The increase of antibacterial activity of the tested antibiotics was observed only when the bovine serum was used as the solvent. As a rule, the increase averaged 50%, but in some instances, the presence of lysozyme dimer resulted in a 100% increase in the activity of the antibiotics.

CONCLUSIONS

Lysozyme dimer (without any conservant) in concentrations of 5 µg/ml exhibits in vitro a synergism with some antibiotics used in MIC (minimal inhibitory concentration) in the presence of bovine serum in inhibiting bacteria growth. The results obtained until now make it clear that further studies will be essential.

EXAMPLE 9

Synergism with AZT in Treating AIDS Patients

Ito et al have recently reported that TNF-α can antagonize the anti-HIV activity of AZT (Ito, M. et al.: "Tumor necrosis factor antagonizes inhibitory effect of azidothymidine on human immunodeficiency virus (HIV) replication in vitro; Biochem. Biophys. Res. Commun. 1990, 166; 1095–1101). AIDS patients in an advanced stage suffer from many occasional infections. Some infective agents may induce elevation of TNF-α, IL-6 and other cytokines that may be either immunosuppressive or may promote HIV replication. Accordingly, treatment with AZT alone is not sufficiently effective. In order to increase the anti-HIV activity of AZT, it is therefore proposed to combine the AZT treatment with the administration of lysozyme dimer to inhibit the synthesis of TNF—the factor antagonizing an anti-HIV activity of AZT.

I claim:

1. A method for modulating natural immunological defensive mechanisms in animals or humans comprising administering to an animal or human body a dimerized form of lysozyme in an amount effective for modulating said defensive mechanisms.

2. The method according to claim 1, wherein the administration of dimerized lysozyme strengthens said defensive mechanisms.

3. The method according to claim 1, wherein said modulation comprises at least one action selected from the group consisting of an inhibition of tumor necrosis factor (TNF) release, a decrease of a TNF level, an enhancement of phagocytosis, and an increase of interferon release.

4. The method according to claim 1, wherein said method is for prophylactic or therapeutic application.

5. The method according to claim 1, wherein the dimerized lysozyme is administered in combination with an antibiotic, said combination being effective for increasing the antibacterial activity of the antibiotic by up to 50% on average in the presence of bovine serum in vitro.

6. The method according to claim 1, wherein said dimerized lysozyme is administered in the form of an injection solution comprising the dimerized lysozyme in an amount of 0.01–10 mg/ml of an apyrogenic sterile composition.

7. The method according to claim 6, wherein the injection solution comprises the dimerized lysozyme in an amount of 0.1–1.0 mg/ml.

8. The method according to claim 1, wherein said dimerized lysozyme is administered in the form of a composition selected from the group consisting of a gel, an ointment, an antiseptic dressing, and a impregnated with dimerized lysozyme.

9. A pharmaceutical composition comprising a dimerized form of lysozyme in combination with an antibiotic, wherein the composition is effective for increasing the antibacterial activity of the antibiotic by up to 50% on average in the presence of bovine serum in vitro.

10. A method of treating a wound on an animal or human body comprising applying lysozyme dimer to the wound.

* * * * *